US00PP13421P2

(12) United States Plant Patent
Bullis

(10) Patent No.: US PP13,421 P2
(45) Date of Patent: Dec. 24, 2002

(54) AECHMEA PLANT NAMED 'DEL MAR'

(75) Inventor: Patricia Gomez Bullis, Princeton, FL (US)

(73) Assignee: Bullis Bromeliads, Inc., Princeton, FL (US)

( * ) Notice: Subject to any disclaimer, the term of this patent is extended or adjusted under 35 U.S.C. 154(b) by 0 days.

(21) Appl. No.: 09/891,422

(22) Filed: Jun. 27, 2001

(51) Int. Cl.[7] ..... A01H 5/00
(52) U.S. Cl. ..... Plt./370

(58) Field of Search ..... Plt./370, 371

*Primary Examiner*—Bruce R. Campell
*Assistant Examiner*—June Hwu
(74) *Attorney, Agent, or Firm*—C. A. Whealy

(57) ABSTRACT

A new and distinct cultivar of Aechmea plant named 'Del Mar', characterized by its compact, upright and outwardly arching growth habit; solid green-colored foliage; inflorescences held upright and above foliage on strong red scapes; tightly branched inflorescences with purple and dark red flower bracts and blue purple and greenish white sepals; and long-lasting inflorescences that maintain flower bract and sepal coloration for about five to seven months.

2 Drawing Sheets

BOTANICAL CLASSIFICATION/CULTIVAR DESIGNATION

*Aechmea fendleri*×*Aechema dichlamydea trinitensis* cultivar Del Mar.

BACKGROUND OF THE INVENTION

The present Invention relates to a new and distinct cultivar of Aechmea plant, botanically known as *Aechmea fendleri*×*Aechmea dichlamydea trinitensis* and referred to by the name 'Del Mar'.

The new Aechmea is a product of a planned breeding program conducted by the Inventor in Princeton, Fla. The objective of the breeding program is to create new Aechmea cultivars with compact plant habit appropriate for container production, desirable inflorescence coloration and good postproduction longevity.

The new Aechmea originated from a cross made by the Inventor in Princeton, Fla. in May, 1994, of an unidentified selection of *Aechmea fendleri*, not patented, as the female, or seed, parent with an unidentified selection of *Aechmea dichlamydea trinitensis*, not patented as the male, or pollen, parent. The cultivar Del Mar was discovered and selected by the Inventor as a flowering plant within the progeny of the stated cross in a controlled environment in Princeton, Fla., in September, 1996.

Asexual reproduction of the new Aechmea by tissue culture in a controlled environment in Princeton, Fla., has shown that the unique features of this new Aechmea are stable and are reproduced true to type in successive generations.

SUMMARY OF THE INVENTION

The new Aechmea has not been observed under all possible environmental conditions. The phenotype may vary somewhat with variations in environment such as temperature, daylength, light intensity, fertilizer rate and type, and/or irrigation amount and frequency without, however, any variance in genotype.

The following characteristics have been repeatedly observed and are determined to be basic characteristics of 'Del Mar' and distinguish 'Del Mar' as a new and distinct cultivar:

1. Compact, upright and outwardly arching growth habit.
2. Solid green-colored foliage.
3. Inflorescences held upright and above foliage on strong red scapes.
4. Tightly branched inflorescences with purple and dark red flower bracts and blue purple and greenish white sepals.
5. Long-lasting inflorescences that maintain flower bract and sepal coloration for about five to seven months.

Compared to plants of the female parent, the unidentified selection of *Aechmea fendleri*, plants of the new Aechmea are more compact, have darker green leaves, and darker blue purple sepals. Compared to plants of the male parent, the unidentified selection of *Aechmea dichlamydea trinitensis*, plants of the new Aechmea are much more compact and have shorter scapes.

Plants of the new Aechmea can be compared to plants of the *Aechmea dichlamydea trinitensis*×*Aechmea fendleri* cultivar Blue Tango, disclosed in U.S. Plant Pat. No. 11,743. In side-by-side comparisons conducted by the Inventor in Princeton, Fla., plants of the new Aechmea differed from plants of the cultivar Blue Tango in the following characteristics:

1. Plants of the new Aechmea are more compact than plants of the cultivar Blue Tango.
2. Plants of the new Aechmea have smaller inflorescences than plants of the cultivar Blue Tango.
3. Plants of the new Aechmea have purple and dark red flower bracts whereas plants of the cultivar Blue Tango have mostly blue purple flower bracts.

BRIEF DESCRIPTION OF THE PHOTOGRAPHS

The accompanying colored photographs illustrate the overall appearance of the new Aechmea, showing the colors as true as it is reasonably possible to obtain in colored reproductions of this type. Colors in the photographs may differ slightly from the color values cited in the detailed botanical description which accurately describe the colors of the new Aechmea.

The photograph on the first sheet comprises a side perspective view of a typical plant of 'Del Mar' that was about 20 months old and grown in a 15-cm container.

The photograph on the second sheet comprises a close-up view of typical leaves and a typical inflorescence of 'Del Mar'.

DETAILED BOTANICAL DESCRIPTION

The following observations, measurements, values, and comparisons describe plants grown in Princeton, Fla., under a polyethylene-covered greenhouse and conditions which closely approximate those used in commercial practice. During the production of the plants, day temperatures ranged from 18 to 35° C., night temperatures ranged from 18 to 24° C., and light levels were about 1,400 foot-candles. Single plants used for this description were about 20 months old and grown in 15-cm containers. Color references are made to The Royal Horticultural Society Colour Chart except where general terms of ordinary dictionary significance are used.

Parentage:

*Female, or seed, parent.*—Unidentified selection of *Aechmea fendleri*, not patented.

*Male, or pollen, parent.*—Unidentified selection of *Aechmea dichlamydea trinitensis.*

Propagation:

*Type.*—By tissue culture.

*Time to initiate roots on tissue-cultured plants.*—Summer: About 30 days at temperatures of 29 to 35° C. Winter: About 60 days at temperatures of 18 to 24° C.

*Time to produce a rooted tissue-cultured plant.*—Summer: About 60 days at temperatures of 29 to 35° C. Winter: About 100 days at temperatures of 18 to 24° C.

*Root description.*—Fine; freely branching.

Plant description:

*General appearance.*—Compact, upright and outwardly arching growth habit. Rosette leaves are erect when young, becoming outwardly arching to drooping with development. Appropriate for 12.5 to 15-cm containers.

*Plant height.*—Soil surface to top of leaf canopy: About 34 cm. Soil surface to top of inflorescence: About 56 cm.

*Plant diameter or spread.*—About 65 cm.

*Growth rate/vigor.*—Moderately vigorous.

*Foliage description.*—Arrangement: Basal rosette, spiral phyllotaxis; sessile. Quantity of leaves per plant: About 36. Shape: Linear. Apex: Cuspidate to aristate. Margin: Entire with very sharp spines; spines about 2 mm in length. Length: About 45 cm. Width: About 6.5 cm. Aspect: Slightly concave. Texture, upper and lower surfaces: Leathery, flexible; thick; smooth and glaucous. Venation: Parallel. Leaf sheath: Not observed. Color: Young leaves, upper surface: 146A; bloom, close to 156A. Young leaves, lower surface: Close to 144A; bloom, close to 156A. Fully expanded leaves, upper surface: 147A; bloom, close to 156A. Fully expanded leaves, lower surface: Close to 146A; bloom, close to 156A. Venation, upper surface: Same as lamina. Venation, lower surface: 146A. Spines: Close to 175A.

Inflorescence description:

*Inflorescence form.*—Terminal inflorescences with tightly branched panicles supported by erect and strong scapes. About 28 lateral panicles each with about 15 to 20 individual flowers. Flowers ovoid in shape; sessile; with purple and dark red flower bracts and blue purple and greenish white sepals.

*Inflorescence longevity.*—Inflorescences of the new Aechmea are very long-lasting; bract and sepal coloration are maintained for about five to seven months. Inflorescences persistent.

*Natural flowering season and time to flower.*—Plants typically flower during the summer and will begin flowering about 8 to 10 weeks after planting.

*Inflorescence size.*—Length: About 22 cm. Width: About 13 cm.

*Lateral panicle size.*—Length: About 6 cm. Diameter: About 2.5 cm.

*Flower size.*—Length: About 2.2 cm. Diameter: About 7 mm.

*Primary bracts.*—Arrangement: Spirally along scape and subtending lower panicles. Shape: Linear; sessile. Apex: Aristate to cuspidate. Length: About 8.3 cm. Width: About 3.3 cm. Texture, upper and lower surfaces: Papery, smooth; glaucous. Color: Upper surface: Close to 144B; bloom, close to 156D; becoming tan, close to 164C to 164D, with subsequent development. Lower surface: 144A to 144B; bloom, close to 156D; becoming tan, close to 164C to 164D, with subsequent development.

*Flower bracts.*—Arrangement: One subtending each flower, closely adhered to sepals. Shape: Rounded, broad; decurrent. Apex: Cuspidate to aristate. Length: About 1.1 cm. Width: About 6 mm. Texture: Smooth, waxy. Color: Towards apex, 79A; towards base, 53B to 53C.

*Sepals.*—Quantity: Two, fused. Shape: Elongate, sharply tapering towards apex. Apex: Acute to apiculate. Length: About 1.7 cm. Width: About 7 mm. Texture: Smooth, waxy. Color: Towards apex, 96A to 96B; towards base, 145C to 145D.

*Petals.*—Interior to sepals, not visible; not united; usually with two scales.

*Reproductive organs.*—Not visible; minute and inconspicuous; green white in color; typical of species.

*Scape.*—Strength: Very strong. Aspect: Typically erect. Length: About 39 cm. Diameter: About 1.2 cm. Texture: Tough, smooth. Color: Close to 53B to 46C.

*Seed.*—Seed production has not been observed.

Temperature tolerance: Plants of the new Aechmea have been observed to tolerate temperatures from about 10 to about 40° C.

Disease resistance: Plants of the new Aechmea have not been observed to resistant to pathogens common to Aechmea.

It is claimed:

1. A new and distinct cultivar of Aechmea plant named 'Del Mar', as illustrated and described.

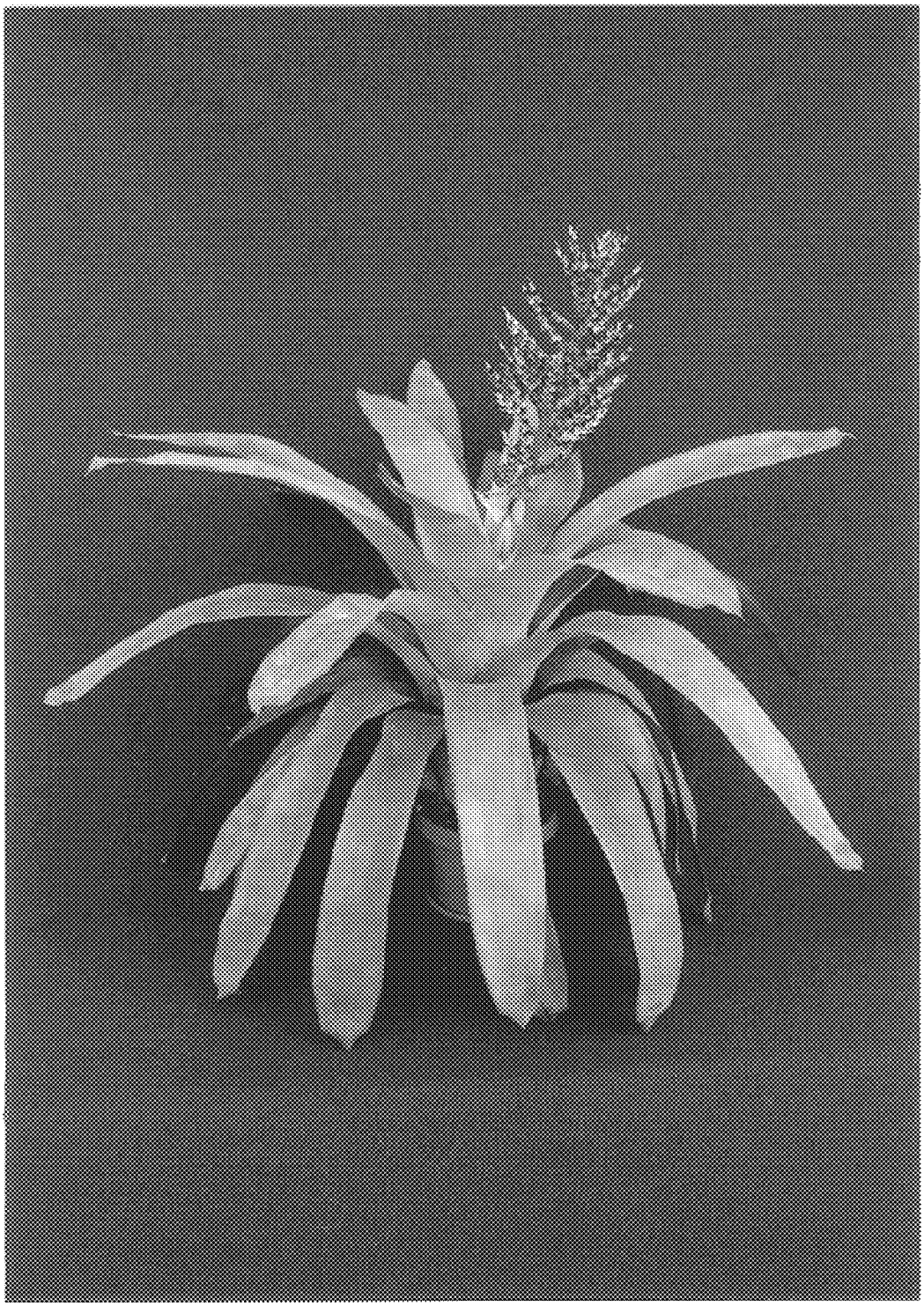

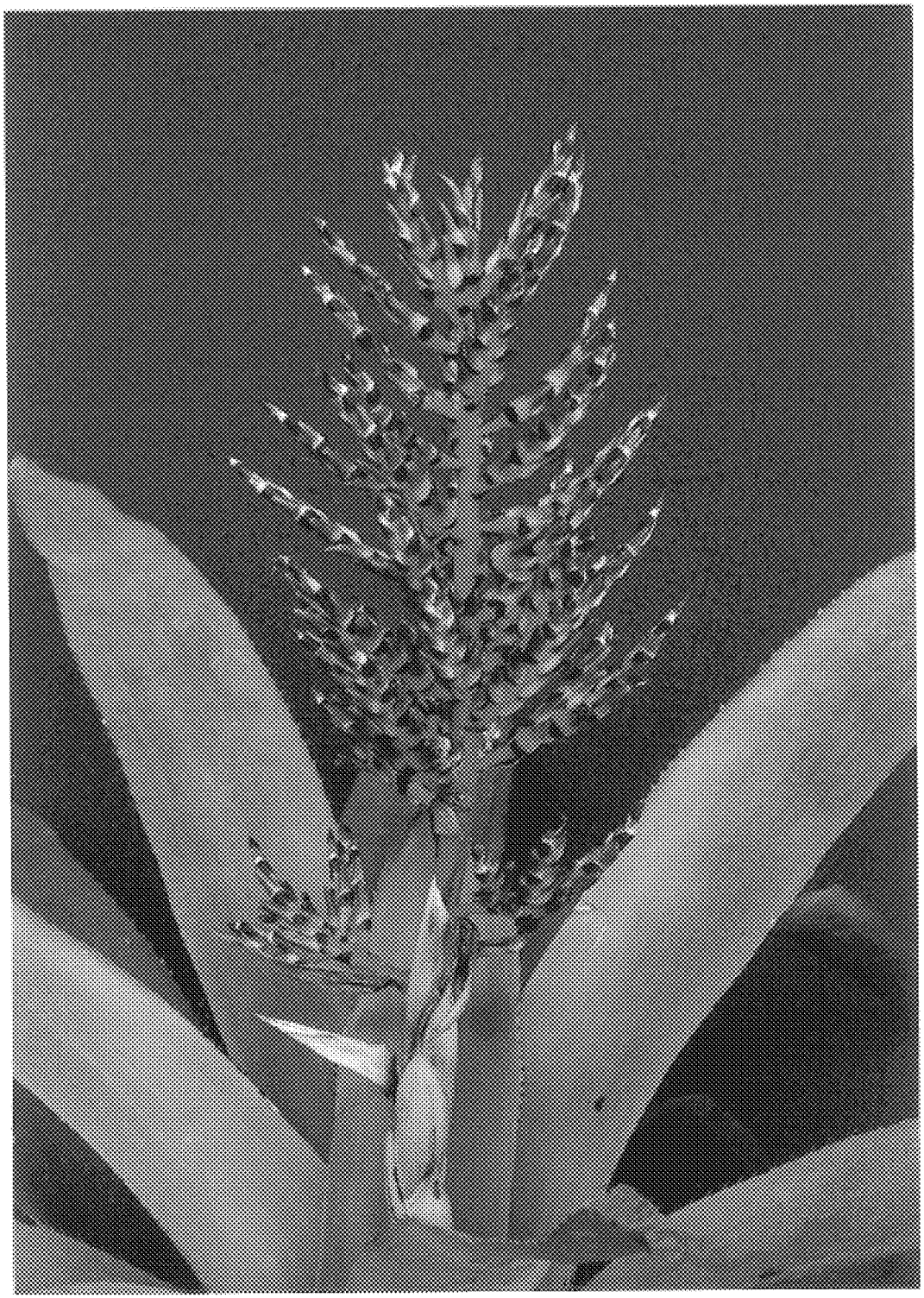

* * * * *